(12) United States Patent
Grove

(10) Patent No.: US 8,637,551 B2
(45) Date of Patent: Jan. 28, 2014

(54) 2-(1,2-BENZISOXAZOL-3-YL)BENZYLAMINE DERIVATIVES

(75) Inventor: Simon James Anthony Grove, Glasgow (GB)

(73) Assignee: Merck Sharp & Dohme B.V., Haarlem (NL)

( * ) Notice: Subject to any disclaimer, the term of this patent is extended or adjusted under 35 U.S.C. 154(b) by 0 days.

(21) Appl. No.: 13/382,608

(22) PCT Filed: Jul. 6, 2010
(Under 37 CFR 1.47)

(86) PCT No.: PCT/EP2010/059621
§ 371 (c)(1),
(2), (4) Date: Apr. 26, 2012

(87) PCT Pub. No.: WO2011/003895
PCT Pub. Date: Jan. 13, 2011

(65) Prior Publication Data
US 2013/0023566 A1    Jan. 24, 2013

(30) Foreign Application Priority Data

Jul. 7, 2009 (EP) .................... 09164724

(51) Int. Cl.
*C07D 261/20* (2006.01)
*A61K 31/423* (2006.01)
(52) U.S. Cl.
USPC ......... 514/338; 546/272.1; 548/241; 514/379
(58) Field of Classification Search
None
See application file for complete search history.

(56) References Cited

U.S. PATENT DOCUMENTS 6,080,773 A    6/2000  Dijcks et al.

FOREIGN PATENT DOCUMENTS

WO    99/18941    4/1999
WO    2009/040027 A1    4/2009

OTHER PUBLICATIONS

WO11003895 Search Report, Sep. 2010.

*Primary Examiner* — Zinna Northington Davis
(74) *Attorney, Agent, or Firm* — Susan L. Hess; John C. Todaro

(57) ABSTRACT

The invention relates to 2-(1,2-benzisoxazol-3-yl)benzylamine derivatives having the general Formula (I) wherein $R_1$ represents the group $CONR_2R_3$ which is present at one of the positions 5-, 6- or 7- on the 1,2-benzisoxazole ring; $R_2$ and $R_3$ are independently H or $(C_{1-4})$alkyl; and $R_4$ is cyclopropyl, 2-pyridyl or phenyl, optionally substituted with one or more halogens; or a pharmaceutically acceptable salt thereof, to pharmaceutical compositions comprising the same, as well as to the use of these derivatives for the treatment of pain, such as neuropathic pain or inflammatory pain.

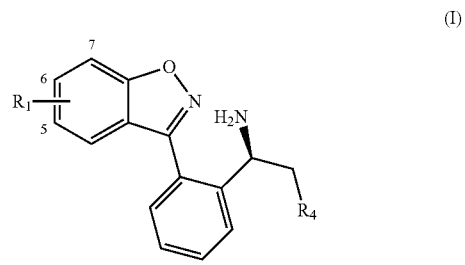

(I)

12 Claims, No Drawings

2-(1,2-BENZISOXAZOL-3-YL)BENZYLAMINE DERIVATIVES

RELATED APPLICATIONS

This application is a national stage entry under 35 U.S.C. §371 of PCT/EP2010/059621 filed on Jul. 6, 2010 which claims priority to EP 09164724.8 filed on Jul. 7, 2009.

This invention relates to 2-(1,2-benzisoxazol-3-yl)benzylamine derivatives, to pharmaceutical compositions comprising the same and to the use of these 2-(1,2-benzisoxazol-3-yl)benzylamine derivatives in the treatment of chronic neuropathic pain.

Neuropathic pain, or the spontaneous pain and abnormal sensitivity following a nerve injury, typically results from a traumatic injury, an infection or disease, or surgery, and can persist long after the initial injury has healed. Current treatment options are limited or inadequate for many people.

HCN channels are the molecular substrates of the currents known as $I_h$, $I_f$ or $I_q$. Hyperpolarization-activated, cyclic nucleotide-gated (HCN) channels, also known as pacemaker channels, first identified in cardiac pacemaker cells (Di Francesco, 1993 Annu Rev Physiol. 55:455-472), have also been found in a variety of peripheral and central neurones (e.g. Notomi & Shigemoto 2004 J. Comp. Neurol. 471: 241-276). These channels are slowly activated by hyperpolarization to generate depolarizing inward current (termed $I_f$ in cardiac cells and $I_h$ in neurones) and are permeable to both sodium and potassium ions. The four HCN channel isoforms are present in pain-processing regions of the nervous system including thalamus, amygdala, spinal cord & primary sensory neurones. It is likely that all four subunits are present in dorsal root ganglia (DRG), with HCN1 having the highest level of expression. This is consistent with the activation kinetics of $I_h$ current recorded from DRG (Tu et al., J Neurosci. Res. 2004 76:713-722).

$I_h$ current has been detected in neurons from many regions of the nervous system involved in nociception, including the substantia gelatinosa of spinal cord, dorsal root ganglia, amygdala, cingulate cortex and the thalamus. $I_h$ currents appear to be preferentially expressed by medium/large DRGs and may be absent from the somata of most C-type (small) DRGs (Scroggs et al., J Neurophysiol. 71: 271-279; Tu et al., J Neurosci. Res. 2004 76:713-722). Furthermore, it has been reported that nerve injury in rats (Chung model) increased $I_h$ current density in large DRGs and caused pacemaker-driven, spontaneous action potentials in the ligated nerve. ZD 7288, an $I_h$ channel blocker, reduced the firing frequency of ectopic discharges in A-beta and A-delta fibres, without causing conduction block (Lee et al 2005 J Pain 417-424).

Intraperitoneal administration of an $I_h$ blocker, ZD 7288, in a model of neuropathic pain, dose-dependently reverses mechanical allodynia (Chung/von Frey; Chaplan, et al 2003 J Neurosci. 23: 1169-1178). ZD 7288 also suppresses allodynia in the rat CFA model of inflammatory pain and blocks spontaneous pain in a rat, mild thermal injury model. Another research group has reported that local administration of ZD 7288 to the sciatic nerve 4 h after surgery in rats attenuates mechanical allodynia in the Brennan model (Dalle & Eisenach 2005 Reg. Anesth. and Pain Med 243-248).

It is hypothesised that, during chronic painful conditions, primary afferents become hyperexcitable due to peripheral sensitisation after inflammation, and a change of ion channel expression at the site of nerve damage associated with neuropathy. ZD 7288-induced inhibition of $I_h$ reduces spontaneous activity in nerve injured myelinated DRG (Yagi et al, 2000 Proc 9th World Congress on Pain 109-117) so reducing the associated pain. Current preclinical data indicate that $I_h$ channel blockers will have utility in the treatment of chronic neuropathic pain.

2-(1,2-Benzisoxazol-3-yl)benzylamine derivatives were disclosed in the International Patent Applications WO 97/40027 (Akzo Nobel N.V.) and WO 99/18941 (Akzo Nobel N.V.) as $I_h$ channel inhibitors useful in the treatment of psychiatric disorders such as depression, anxiety and psychosis. Whilst these 2-(1,2-benzisoxazol-3-yl)benzylamine derivatives were found active in animal models wherein peripheral nerve injury causes neuropathic pain (Chung model for neuropathic pain), these compounds with high CNS (central nervous system) penetration cause side effects such as ataxia and tremors at doses (multiple <2) similar to those causing efficacy in rodents.

There remains a need for $I_h$ channel inhibitors having a preferential peripheral activity.

To this end the present invention provides 2-(1,2-benzisoxazol-3-yl)benzylamine derivatives having the general Formula I

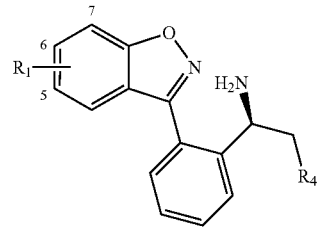

Formula I wherein
$R_1$ represents the group $CONR_2R_3$ which is present at one of the positions 5-, 6- or 7- on the 1,2-benzisoxazole ring;
$R_2$ and $R_3$ are independently H or $(C_{1-4})$alkyl; and
$R_4$ is cyclopropyl, 2-pyridyl or phenyl, optionally substituted with one or more halogens;
or a pharmaceutically acceptable salt thereof.

The compounds of the invention, which differ in structure from the closest prior art (WO 97/40027) compounds in the presence of the carboxamide group $CONR_2R_3$, were surprisingly found to have restricted CNS penetration and were found effective in the in vivo neuropathic pain (Chung) model at doses where CNS side effects were not observed (even at dose multiple >5).

The term $(C_{1-4})$alkyl as used in the definition of Formula I means a branched or unbranched alkyl group having 1-4 carbon atoms, like butyl, isobutyl, tertiary butyl, propyl, isopropyl, ethyl and methyl. Preferred is methyl.

The term halogen means F, Cl, Br or I. A preferred halogen is F. The term 2-pyridyl as used in the definition of Formula I means a pyridine ring where the alkyl chain is bonded to the carbon next to the nitrogen.

Preferred are 2-(1,2-benzisoxazol-3-yl)benzylamine derivatives of formula I wherein $R_1$ represents the group $CONR_2R_3$ at the 6-position on the 1,2-benzisoxazole ring.

Further preferred are compounds of formula I $R_2$ and $R_3$ are both methyl or hydrogen, most preferably $R_2$ and $R_3$ are both hydrogen.

The 2-(1,2-benzisoxazol-3-yl)benzylamine derivatives of the invention are single enantiomers having the (S)-configuration.

One embodiment of the invention provides 2-(1,2-benzisoxazol-3-yl)benzylamine derivatives having the general Formula I Formula I

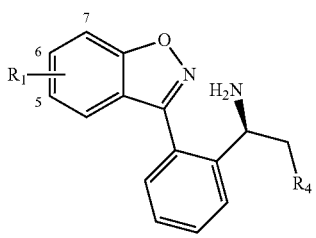

wherein
R₁ represents the group $CONR_2R_3$ which is present at one of the positions 5-, 6- or 7- on the 1,2-benzisoxazole ring;
R₂ and R₃ are independently H or $(C_{1-4})$alkyl; and
R₄ is cyclopropyl:
or a pharmaceutically acceptable salt thereof.

Another embodiment of the invention provides provides 2-(1,2-benzisoxazol-3-yl)benzylamine derivatives having the general Formula I Formula I

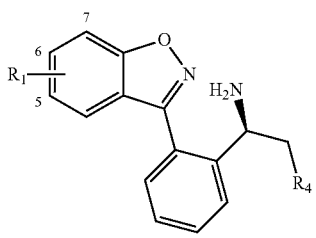

wherein
R₁ represents the group $CONR_2R_3$ which is present at one of the positions 5-, 6- or 7- on the 1,2-benzisoxazole ring;
R₂ and R₃ are independently H or $(C_{1-4})$alkyl; and
R₄ is 2-pyridyl;
or a pharmaceutically acceptable salt thereof.

Yet another embodiment of the invention provides 2-(1,2-benzisoxazol-3-yl)benzylamine derivatives having the general Formula I Formula I

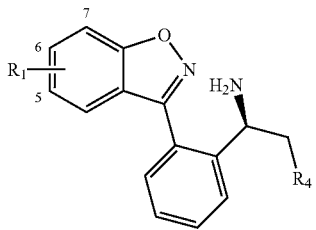

wherein
R₁ represents the group $CONR_2R_3$ which is present at one of the positions 5-, 6- or 7- on the 1,2-benzisoxazole ring;
R₂ and R₃ are independently H or $(C_{1-4})$alkyl; and
R₄ is phenyl, optionally substituted with one or more halogens;
or a pharmaceutically acceptable salt thereof.

Specifically preferred is a 2-(1,2-benzisoxazol-3-yl)benzylamine derivative which is selected from:
3-(2-(1-(S)-amino-2-(pyridin-2-yl)ethyl)phenyl)benzo[d]isoxazole-6-carboxamide;
3-(2-((S)-1-amino-2-phenylethyl)phenyl)benzo[d]isoxazole-6-carboxamide;
3-(2-(1-(S)-amino-2-(pyridin-2-yl)ethyl)phenyl)-N,N-dimethylbenzo[d]isoxazole-6-carboxamide;
3-(2-(1-(S)-amino-2-(pyridin-2-yl)ethyl)phenyl)-N,N-dimethylbenzo[d]isoxazole-7-carboxamide;
3-(2-(1-(S)-amino-2-cyclopropylethyl)phenyl)benzo[d]isoxazole-6-carboxamide; and
3-(2-(1-(S)-amino-2-(pyridin-2-yl)ethyl)phenyl)benzo[d]isoxazole-7-carboxamide;
or a pharmaceutically acceptable salt thereof.

The 2-(1,2-benzisoxazol-3-yl)benzylamine derivatives of the invention may be prepared by methods known in the art of organic chemistry in general.

Formula 2

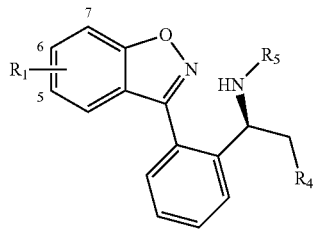

2-(1,2-Benzisoxazol-3-yl)benzylamine derivatives having the general Formula I, wherein R₁-R₄ have the meaning as previously defined, can be prepared from compounds of Formula 2 where R₅ is a protecting group such as a tert-butoxycarbonyl (BOC), benzyloxycarbonyl (CBZ), trichloroethoxycarbonyl (TROC), (R)- or (S)-tert-butylsulfinyl and (R)- or (S)-p-toluenesulfinyl. Deprotection steps are well known to those skilled in the art. Methods described in Wuts P. G. M and Greene T. W. 'Protecting Groups in Organic Synthesis' New York, Wiley (2006) may be used. Compounds of Formula 1 can be prepared from compounds of Formula 2 where R₅ is a sulfinyl group of formula $SOR_7$ where R₇ is an alkyl or optionally substituted aryl group such as an (R)- or (S)-tert-butyl sulfinyl or (R)- or (S)-p-toluenesulfinyl. Such methods include using an acid, for example, hydrochloric acid in an alcoholic solvent such as methanol. Such methods are well described in the literature, for example the methods described in M. Wakayama and J. Ellman *J. Org. Chem.* 2009, 74, 2646-2650.

Compounds of Formula 1 can be prepared from compounds of Formula 3 where R₅ is a hydrogen atom and R₆ is an alkyl group using a reagent of formula $HNR_2R_3$, wherein R₂ and R₃ have the meaning as previously defined. Such direct displacements of the ester to give an amide may be performed at elevated temperature or with Lewis acid catalysis. Such methods are well known to those skilled in the art. Methods described in March J. 'Advanced Organic Chemistry' New York, Wiley (2007) may be used.

Formula 3

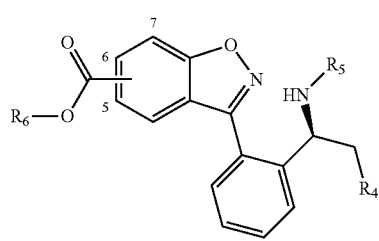

Compounds of Formula 2 where $R_1$ is an amide group, at one of the positions 5-, 6- or 7 of formula $CONR_2R_3$, wherein $R_2$ and $R_3$ are independently H or ($C_{1-4}$)alkyl, can be prepared from a compound of Formula 3 where $R_6$ is a hydrogen atom and an amine reagent of formula $HNR_2R_3$ using standard amide coupling conditions such as formation of an acid chloride using thionyl chloride or oxalyl chloride or generating an activated carbonyl species using a reagent such as 1,1-carbonyldiimidazole or dicyclohexyl-carbodiimide followed by treatment with the amine reagent of formula $HNR_2R_3$ in a solvent such as N-methyl pyrrolidinone or dichloromethane. Such methods are well known to those skilled in the art. Methods described in March J. 'Advanced Organic Chemistry' New York, Wiley (2007) may be used.

Compounds of Formula 2 where $R_1$ is an amide group, at one of the positions 5-, 6- or 7, of formula $CONR_2R_3$ can be prepared from a compound of Formula 3 where $R_6$ is an alkyl group and a reagent of formula $HNR_2R_3$. Such direct displacements of the ester to give an amide may be performed at elevated temperature or with Lewis acid catalysis. Such methods are well known to those skilled in the art. Methods described in March J. 'Advanced Organic Chemistry' New York, Wiley (2007) may be used.

Formula 4

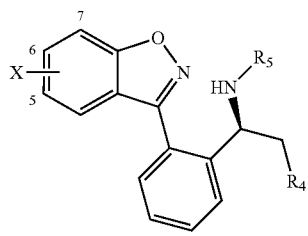

Compounds of Formula 2 where $R_1$ is an amide group, at one of the positions 5-, 6- or 7, of formula $CONR_2R_3$ where $R_2$ and $R_3$ are independently H or ($C_{1-4}$)alkyl can be prepared from a compound of Formula 4 where X is a halo atom, preferably bromo or iodo, at one of the positions 5-, 6- or 7-, and $R_5$ is a protecting group such as a tert-butoxycarbonyl (BOC), benzyloxycarbonyl (CBZ), trichloroethoxycarbonyl (TROC), (R)- or (S)-tert-butylsulfinyl and (R)- or (S)-p-toluenesulfinyl by an amino carbonylation reaction using an amine of formula $HNR_2R_3$ where $R_2$ and $R_3$ are independently H or ($C_{1-4}$)alkyl, carbon monoxide and a transition metal catalyst such as tetrakis(triphenyl-phosphine)palladium (0) or 1,1'-bis(diphenylphosphino)ferrocenedichloropalladium (II).

Formula 5

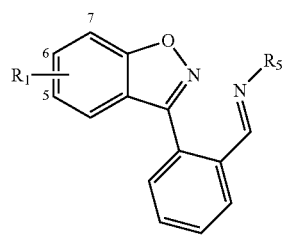

Formula 6

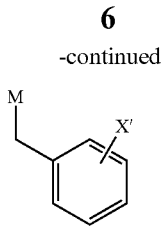

Compounds of Formula 2 where $R_1$ is an amide group, at one of the positions 5-, 6- or 7, of formula $CONR_2R_3$ where one or both of $R_2$ and $R_3$ are a hydrogen atom and $R_4$ is phenyl, optionally substituted with one or more halogen atoms, can be prepared from compounds of Formula 5 where $R_5$ is a chiral auxiliary such as a single enantiomer sulfinyl group of formula $SOR_7$ where $R_7$ is an alkyl or optionally substituted aryl group by the addition of reagent of Formula 6 where M is a metal species such as a magnesium halide or lithium and X' is H or one or more halogen atoms. Compounds of Formula 2 where $R_4$ is phenyl, optionally substituted with one or more halogen atoms, can be isolated as a single diastereomer by separation of the desired diastereomer from the other, undesired diastereomer by chromatography or crystallisation.

Formula 7

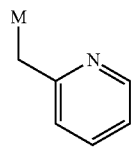

Compounds of Formula 2 where $R_1$ is an amide group, at one of the positions 5-, 6- or 7, of formula $CONR_2R_3$ with one or both of $R_2$ and $R_3$ being a hydrogen atom and $R_4$ is 2-pyridyl can be prepared from compounds of Formula 5 where $R_5$ is a chiral auxiliary such as an (R)- or (S)-sulfinyl group of formula $SOR_7$ where $R_7$ is an alkyl or optionally substituted aryl group by the addition of reagent of Formula 7 where M is a metal species such as a magnesium halide or lithium. Compounds of Formula 2 where $R_4$ is 2-pyridyl can be isolated as a single diastereomer by separation of the desired diastereomer from the other, undesired diastereomer by chromatography or crystallisation.

Compounds of Formula 3 where $R_6$ is a hydrogen atom can be prepared from compounds of Formula 4 where X is a halo atom, preferably bromo or iodo, at one of the positions 5-, 6- or 7-, and $R_5$ is a protecting group such as a tert-butoxycarbonyl (BOC), benzyloxycarbonyl (CBZ), trichloroethoxycarbonyl (TROC), (R)- or (S)-tert-butylsulfinyl or (R)- or (S)-p-toluenesulfinyl by metallating the an alkyl metal reagent such as n-butyl lithium in a solvent such as diethyl ether or tetrahydrofuran temperature less than 0° C. followed by reaction of the intermediate metal species with carbon dioxide. Such metal-halogen exchange reactions may be performed by initial deprotonation of the acidic NH moiety by the use of a strong base such as sodium hydride.

Compounds of Formula 3 where $R_5$ is a protecting group such as a tert-butoxycarbonyl (BOC), benzyloxycarbonyl (CBZ), trichloroethoxycarbonyl (TROC), (R)- or (S)-tert-butylsulfinyl or (R)- or (S)-p-toluenesulfinyl and $R_6$ is a hydrogen atom can be prepared from compounds of Formula 3 where $R_5$ is defined as above and $R_6$ is an alkyl group by saponification using for example a hydroxide source such as aqueous sodium hydroxide in a solvent such as methanol or tetrahydrofuran.

Compounds of Formula 3 where $R_6$ is an alkyl group can be prepared from a compound of Formula 4 where X is a halo, preferably bromo or iodo, at one of the positions 5-, 6- or 7, $R_4$ is phenyl optionally substituted with one or more halogen atoms or 2-pyridyl or cyclopropyl and $R_5$ is a protecting group such as a tert-butoxycarbonyl (BOC), benzyloxycarbonyl (CBZ), trichloroethoxycarbonyl (TROC), (R)- or (S)-tert-butylsulfinyl and (R)- or (S)-p-toluenesulfinyl by an alkoxy carbonylation reaction using an alcohol of formula $R_6OH$ where $R_6$ is an alkyl group, carbon monoxide and a transition metal catalyst such as tetrakis(triphenylphosphine)palladium (0) or 1,1'-bis(diphenylphosphino) ferrocenedichloropalladium (II).

Compounds of Formula 3 where $R_6$ is an alkyl group and $R_5$ is a hydrogen atom can be prepared from compounds of Formula 3 where $R_5$ is a protecting group such as a tert-butoxycarbonyl (BOC), benzyloxycarbonyl (CBZ), trichloroethoxycarbonyl (TROC), (R)- or (S)-tert-butylsulfinyl and (R)- or (S)-p-toluenesulfinyl. Such deprotection steps are well known to those skilled in the art. Methods described in Wuts P. G. M and Greene T. W. 'Protecting Groups in Organic Synthesis' New York, Wiley (2006) may be used.

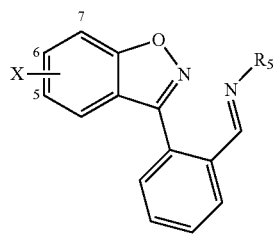

Formula 8

Compounds of Formula 4 where X is a halo, preferably bromo or iodo, at one of the positions 5-, 6- or 7, and $R_4$ is phenyl optionally substituted with one or more halogen atoms can be prepared from compounds of Formula 8 where $R_5$ is a chiral auxiliary such as an (R)- or (S)-sulfinyl group of formula $SCAR$, where $R_7$ is an alkyl, preferably t-butyl, or optionally substituted aryl group by the addition of reagent of Formula 6 where M and X' are as defined above. Compounds of Formula 4 where $R_4$ is phenyl optionally substituted with one or more halogen atoms and $R_5$ is a chiral auxiliary such as an (R)- or (S)-sulfinyl group of formula SCAR, where $R_7$ is an alkyl, preferably t-butyl, or optionally substituted aryl group can be isolated as a single diastereomer by separation of the desired diastereomer from the other, undesired diastereomer by chromatography or crystallisation.

Compounds of Formula 4 where X is a halo, preferably bromo or iodo, at one of the positions 5-, 6- or 7, and $R_4$ is 2-pyridyl can be prepared from compounds of Formula 5 where $R_5$ is a chiral auxiliary such as an (R)- or (S)-sulfinyl group of formula $SOR_7$ where $R_7$ is an alkyl, preferably t-butyl, or optionally substituted aryl group by the addition of reagent of Formula 7 where M is a metal species such as a magnesium halide or lithium. Compounds of Formula 4 where $R_4$ is 2-pyridyl and $R_5$ is a chiral auxiliary such as an (R)- or (S)-sulfinyl group of formula SCAR, where $R_7$ is an alkyl, preferably t-butyl, or optionally substituted aryl group can be isolated as a single diastereomer by separation of the desired diastereomer from the other, undesired diastereomer by chromatography or crystallisation.

Compounds of Formula 4 where X is a halo, preferably bromo or iodo, at one of the positions 5-, 6- or 7, and $R_4$ is phenyl optionally substituted with one or more halogen atoms or $R_4$ is 2-pyridyl or $R_4$ is cyclopropyl and $R_5$ is a protecting group such as a tert-butyloxycarbonyl (BOC) group can be prepared from compounds of Formula 9, where X and $R_4$ have the meanings above, using protection methods well known to those skilled in the art such as those described in Wuts P. G. M and Greene T. W. 'Protecting Groups in Organic Synthesis' New York, Wiley (2006) may be used.

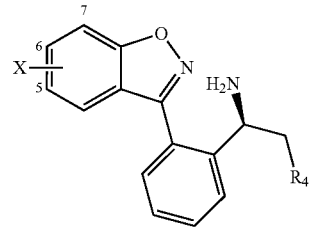

Formula 9

Compounds of Formula 1, 2, 3, 4 and 9 where $R_1$ is an amide group, at one of the positions 5-, 6- or 7-, of formula $CONR_2R_3$, where $R_2$ and $R_3$ are independently H or $(C_{1-4})$ alkyl, $R_4$ is phenyl optionally substituted with one or more halogen atoms or 2-pyridyl or cyclopropyl, $R_5$ is a protecting group such as a tert-butoxycarbonyl (BOC), benzyloxycarbonyl (CBZ) and trichloroethoxycarbonyl (TROC) and X is a halo, preferably bromo or iodo, at one of the positions 5-, 6- or 7, can be isolated as single enantiomers from the corresponding racemic compounds of Formula 10, 11, 12 and 13 respectively where X, $R_1$, $R_4$ and $R_5$ have the meanings above by methods well known to those skilled in the art. These methods include separation of the required enantiomer by high performance liquid chromatography with a chiral stationary phase, supercritical fluid chromatography (SFC) with a chiral stationary phase and resolution of diastereomeric salts using homochiral acids or bases by selective crystallisation.

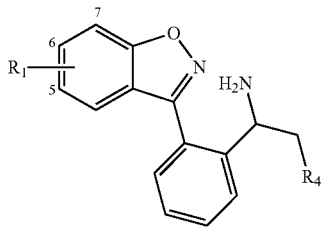

Formula 10

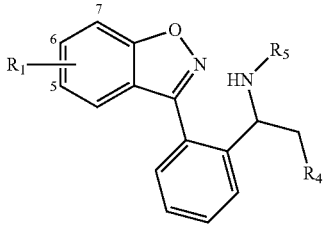

Formula 11

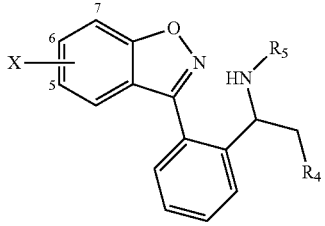

Formula 12

Formula 13

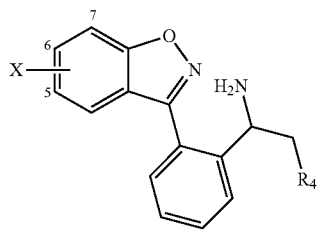

Compounds of Formula 10 where $R_4$ is phenyl optionally substituted with one or more halogen atoms or $R_4$ is cyclopropyl may be prepared from compounds of Formula 14 where $R_1$ is defined as above and Ar is an aromatic ring such as phenyl optionally substituted with one or more halogen atoms by treatment with a base such as potassium tert-butoxide in a solvent such as tetrahydrofuran at a temperature between −78° C. and ambient temperature followed by the addition of a reagent of Formula 15 where LG is a leaving group such as a halogen preferably bromo or iodo or a sulfonate such as a tosylate group and $R_4$ is phenyl optionally substituted with one or more halogen atoms or $R_4$ is cyclopropyl. After the addition of the base and addition of a compound of Formula 14 the reaction is acidified, to hydrolyse the intermediate imine, then basified in order to isolate the desired product.

In a similar manner compounds of Formula 13 where $R_4$ is phenyl optionally substituted with one or more halogen atoms or $R_4$ is cyclopropyl may be prepared from compounds of Formula 16 where X and Ar have the meanings above and a compound of Formula 15 where $R_4$ is phenyl optionally substituted with one or more halogen atoms or $R_4$ is cyclopropyl.

Formula 14

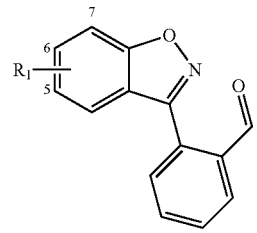

Formula 15

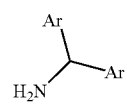

Formula 16

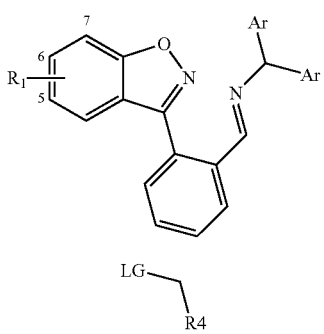

Compounds of Formula 14 can be prepared from compounds of Formula 17 where $R_1$ is an amide group, at one of the positions 5-, 6- or 7, of formula $CONR_2R_3$ where $R_2$ and $R_3$ are independently H or $(C_{1-4})$alkyl by condensing with an amine of Formula 18. Such methods are well known to those skilled in the art and include, for example using anhydrous magnesium sulphate as a dehydrating agent in a solvent such as dichloromethane.

Formula 17

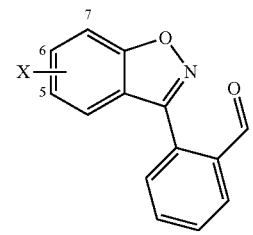

Formula 18

Compounds of Formula 16 can be prepared from compounds of Formula 19 where X is a halo, preferably bromo or iodo, at one of the positions 5-, 6- or 7- by condensing with an amine of Formula 18. Such methods are well known to those skilled in the art and include, for example using magnesium sulphate as a dehydrating agent in a solvent such as dichloromethane.

Formula 19

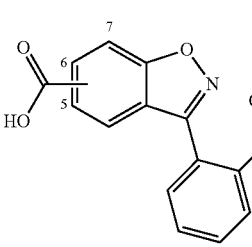

Formula 20

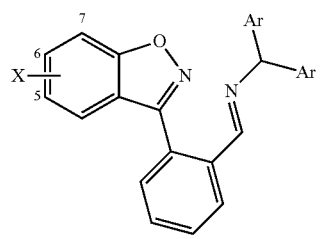

Compounds of Formula 17 where $R_1$ is an amide group, at one of the positions 5-, 6- or 7, of formula $CONR_2R_3$ can be prepared from compounds of Formula 20 where the carboxylic acid moiety is at one of the positions 5-, 6- or 7- on the benzisoxazole ring by condensing with an amine reagent of formula $HNR_2R_3$ where $R_2$ and $R_3$ are independently H or $(C_{1-4})$alkyl using standard amide coupling conditions such as formation of an acid chloride using thionyl chloride or oxalyl chloride or generating an activated carbonyl species using a reagent such as 1,1-carbonyldiimidazole followed by treatment with the amine reagent of formula $HNR_2R_3$ in a solvent such as N-methyl pyrrolidinone or dichloromethane. Such methods are well known to those skilled in the art. Methods described in March J. 'Advanced Organic Chemistry' New York, Wiley (2007) may be used.

Formula 21

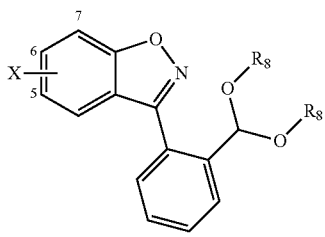

Formula 22

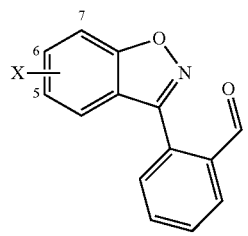

Compounds of Formula 20 can be prepared from compounds of Formula 21 where $R_8$ is an alkyl or aryl group or both $R_8$ groups are bonded together form a alkyl ring system and where X is a halo atom, preferably bromo or iodo, at one of the positions 5-, 6- or 7-, by metal-halogen exchange using an alkyl metal reagent for example n-butyl lithium in a solvent such as diethylether at low temperature, preferably less than 0° C., followed by quenching the metal species with carbon dioxide. Reaction work up with the addition of an acidic hydrolysis step if necessary gives the desired product.

Compounds of Formula 21 can be prepared from compounds of Formula 22 by methods well known to those skilled in the art and described in March J. 'Advanced Organic Chemistry' New York, Wiley (2007), examples include the use of a trialkyl orthoformate of general formula $CH(OR_8)_3$ in the presence of an acid catalyst such as p-toluene sulfonic acid.

Compounds of Formula 5 where $R_5$ is a chiral auxiliary such as an (R)- or (S)-sulfinyl group of formula $SOR_7$ where $R_7$ is an alkyl, preferably tert-butyl or optionally substituted aryl group can be prepared by condensing a compound of Formula 17 where $R_1$ is an amide group, at one of the positions 5-, 6- or 7, of formula $CONR_2R_3$ where $R_2$ and $R_3$ are independently H or $(C_{1-4})$alkyl by condensing with an amine of $R_5NH_2$. A method such as using magnesium sulphate or titanium tetraethoxide as a dehydrating agent in a solvent such as dichloromethane or tetrahydrofuran or a method referenced in P. Zhou et al, *Tetrahedron*, 2004, 60, 8003.

Compounds of Formula 8 where $R_5$ is a chiral auxiliary such as an (R)- or (S)-sulfinyl group of formula $SOR_7$ where $R_7$ is an alkyl, preferably tert-butyl or optionally substituted aryl group can be prepared by condensing compounds of Formula 22 where X is a halo atom, preferably bromo or iodo, at one of the positions 5-, 6- or 7-, with an amine of formula $NH_2R_5$ where $R_5$ has the definition above. Such methods are well known to those skilled in the art and include, for example using anhydrous magnesium sulphate or titanium tetraethoxide as a dehydrating agent in a solvent such as dichloromethane in a or tetrahydrofuran.

Compounds of Formula 22 can be prepared using methods of the prior art such as those described in WO 97/40027 (Akzo Nobel N.V.).

The 2-(1,2-benzisoxazol-3-yl)benzylamine derivatives of Formula I having the (S)-configuration and their salts, may contain an additional centre of chirality, and may exist therefore as stereoisomers, including diastereomers. The present invention includes the aforementioned stereoisomers within its scope and each of the individual R/S and S/S isomers of the compounds of Formula I and their salts, substantially free, i.e. associated with less than 5%, preferably less than 2%, in particular less than 1% of another stereoisomer, and mixtures of such stereoisomers in any proportions.

Purified stereoisomers can be obtained using methods such as cystallisation of chiral salt forms, chiral chromatographic resolution or resolution using enzymatic methods. Such methods are well known to those skilled in the art. Methods described in '*Advanced Organic Chemistry*' (March J., New York, Wiley (1985) and in "*Chirality in Industry*" (Edited by A. N. Collins, G. N. Sheldrake and J. Cosby, 1992; John Wiley) may be used.

The present invention also embraces isotopically-labelled 2-(1,2-benzisoxazol-3-yl)benzylamine derivatives of Formula I of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $_{18}F$, and $^{36}Cl$, respectively. Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Pharmaceutically acceptable salts may be obtained by treating a free base of a compound of Formula I with a mineral acid such as hydrochloric acid, hydrobromic acid, phosphoric acid and sulfuric acid, or an organic acid such as for example ascorbic acid, citric acid, tartaric acid, lactic acid, maleic acid, malonic acid, fumaric acid, glycolic acid, succinic acid, propionic acid, acetic acid and methane sulfonic acid. Preferred are the salts obtained by hydrochloric acid and L-(+)-tartaric acid.

The compounds of the invention may exist in unsolvated as well as in solvated forms with pharmaceutically acceptable solvents such as water, ethanol and the like. In general, the solvated forms are considered equivalent to the unsolvated forms for the purpose of the invention.

The present invention further provides pharmaceutical compositions comprising a 2-(1,2-benzisoxazol-3-yl)benzylamine derivative according to general Formula I, or a pharmaceutically acceptable salt thereof, in admixture with pharmaceutically acceptable auxiliaries, and optionally other therapeutic agents. The term "acceptable" means being compatible with the other ingredients of the composition and not deleterious to the recipients thereof. Compositions include e.g. those suitable for oral, sublingual, subcutaneous, intravenous, epidural, intrathecal, intramuscular, transdermal, pulmonary, local, ocular or rectal administration, and the like, all in unit dosage forms for administration. A preferred route of administration is the oral route.

For oral administration, the active ingredient may be presented as discrete units, such as tablets, capsules, powders, granulates, solutions, suspensions, and the like. For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al, Remington: *The Science and Practice of Pharmacy* (20th Edition, Lippincott Williams & Wilkins, 2000, see especially Part 5: Pharmaceutical Manufacturing), the active agent may be compressed into solid dosage units, such as pills, tablets, or be processed into capsules, suppositories or patches. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as described before, in combination with packaging material suitable for said composition, said packaging material including instructions for the use of the composition for the use as described before.

The 2-(1,2-benzisoxazol-3-yl)benzylamine derivatives of the invention were found to be inhibitors of the $I_h$ channel as measured by patch clamp electrophysiology using the human HCN1 channel (see international patent application WO 01/090142:" Full length human HCN1 $I_h$ channel subunits and variants"—Akzo Nobel N.V.) expressed in HEK cells.

The compounds of the invention have utility in the treatment of pain which is mediated through modulation of the $I_h$ channel, preferably neuropathic or inflammatory pain, such as neuropathic pain occurring in conditions like trigeminal neuralgia, post herpetic neuralgia (pain following shingles), diabetic neuropathy, phantom limb pain following amputation, multiple sclerosis, pain following chemotherapy, fibromyalgia (chronic muscle pain disorder), HIV infection, alcoholism, cancer (as a direct result of cancer on peripheral nerves or as a side effect of some chemotherapy drugs) and atypical facial pain.

The compounds of the invention can also be used in conjunction with other drugs, for example analgesic drugs such as opioids and non-steroidal anti-inflammatory drugs (NSAIDs), including COX-2 selective inhibitors.

The compounds of the invention may be administered to humans in a sufficient amount and for a sufficient amount of time to alleviate the symptoms. Illustratively, dosage levels for humans can be in the range of 0.001-50 mg per kg body weight, preferably in a dosage of 0.01-20 mg per kg body weight.

EXPERIMENTAL

Compound 1a: (4-bromo-2-fluorophenyl)(2-(diethoxymethyl)phenyl)methanol

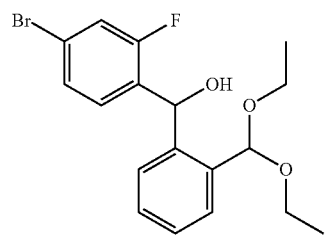 [SMILES: CCOC(OCC)c1ccccc1C(O)c1ccc(Br)cc1F]

To a mechanically stirred solution of 1-bromo-2-(diethoxymethyl)benzene (266 g) in dry diethyl ether (1.5 ) cooled to −70° C. under nitrogen was added a 2.5M solution of n-butyl lithium in hexanes (414 mL) dropwise over 30 min. The reaction mixture was stirred at a temperature less than −60° C. for 45 min then a solution of 4-bromo-2-fluorobenzaldehyde in dry diethyl ether (1.5 ) was added dropwise over 1 h maintaining the low temperature. The cooling bath was removed allowing the reaction to warm to +10° C. over 3 h. The reaction was quenched by the addition of water (500 mL). Organic layer was separated and the aqueous layer washed with ethyl acetate (2×500 mL). Combined organic layers were washed with brine then dried over anhydrous sodium sulfate and evaporated to yield the title product (371.1 g) as a yellow oil.

In a similar manner was prepared starting from 3-bromo-2-fluorobenzaldehyde:

Compound 1b: (3-bromo-2-fluorophenyl)(2-(diethoxymethyl)phenyl)methanol

Compound 2a: (4-bromo-2-fluorophenyl)(2-(diethoxymethyl)phenyl)methanone

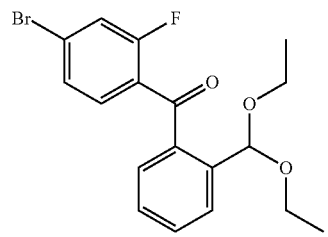 [SMILES: CCOC(OCC)c1ccccc1C(=O)c1ccc(Br)cc1F]

(4-bromo-2-fluorophenyl)(2-(diethoxymethyl)phenyl)methanol (Compound 1a) (116 g) was dissolved in t-butanol (680 mL) with stirring and to the resulting solution was added water (1.4 ) followed by sodium bicarbonate (54.2 g). Using a water bath used to keep temperature around 20° C., 1,3-dibromo-5,5-dimethylhydantoin (48.3 g) and then TEMPO (0.51 g) was added and the cloudy yellow coloured suspension stirred at room temperature overnight. Saturated sodium bicarbonate (360 mL) and sodium thiosulfate (48 g in water) was added. The resulting mixture was stirred for 10 min then extracted with ethyl acetate, the extracts were washed with brine, dried over anhydrous sodium sulfate and evaporated to give the title product (118 g) as a dark yellow oil.

In a similar manner was prepared starting from (3-bromo-2-fluorophenyl)(2-(diethoxymethyl)phenyl)methanol (Compound 1 b): Compound 2b (3-bromo-2-fluorophenyl)(2-(diethoxymethyl)phenyl)methanone Compound 3a: (4-bromo-2-(propan-2-ylideneaminooxy)phenyl)(2-(diethoxymethyl) phenyl)methanone

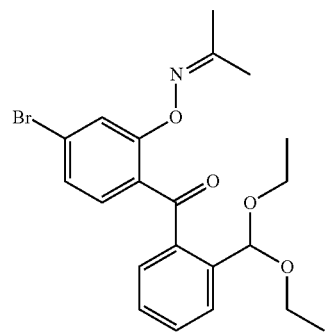 [SMILES: CCOC(OCC)c1ccccc1C(=O)c1ccc(Br)cc1ON=C(C)C]

To a mechanically stirred solution of acetone oxime (20.33 g) in tetrahydrofuran (500 mL) under nitrogen was added a solution of 1M potassium tert-butoxide in tetrahydrofuran (325 mL) while cooling in an ice water bath. The thick white suspension was stirred at 20° C. for 20 min then a solution of (4-bromo-2-fluorophenyl)(2-(diethoxymethyl)phenyl) methanone (Compound 2a) (118 g) in tetrahydrofuran (400 mL) was added over 20 min and the resulting pale orange suspension stirred at room temperature for 1 h then refluxed for 2 h. The reaction mixture was diluted with water (680 mL) and extracted into ethyl acetate. The combined organic layers were washed with brine, dried over anhydrous magnesium sulfate and evaporated to give the title compound (116 g).

In a similar manner was prepared starting from (3-bromo-2-fluorophenyl)(2-(diethoxymethyl)phenyl)methanone (Compound 2b): Compound 3b (3-bromo-2-(propan-2-ylideneaminooxy)phenyl)(2-(diethoxymethyl) phenyl)methanone Compound 4a: 2-(6-bromobenzo[d]isoxazol-3-yl)benzaldehyde

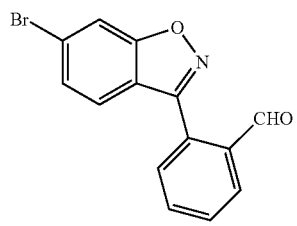

To a stirred solution of (4-bromo-2-(propan-2-ylideneaminooxy)phenyl)(2-(diethoxymethyl)phenyl)methanone (Compound 3a) (18 g) in ethanol (50 mL) at 70° C. was added 2M hydrochloric acid (25 mL). The mixture was stirred at 70° C. for 20 min forming a thick suspension. Water (500 mL) was added and the resultant solid filtered off and dried in vacuo at 50° C. to give the title compound (12 g).

In a similar manner was prepared starting from (3-bromo-2-(propan-2-ylideneaminooxy)phenyl)(2-(diethoxymethyl) phenyl)methanone (Compound 3b):

Compound 4b: 2-(7-bromobenzo[d]isoxazol-3-yl)benzaldehyde

Compound 5: 6-bromo-3-(2-(diethoxymethyl)phenyl)benzo[d]isoxazole

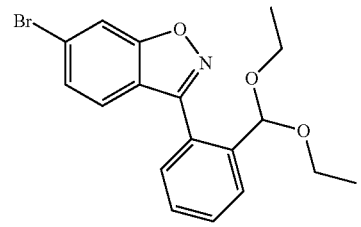 [SMILES: CCOC(OCC)c1ccccc1-c1noc2cc(Br)ccc12]

To a stirred suspension of 2-(6-bromobenzo[d]isoxazol-3-yl)benzaldehyde (Compound 4a) (10 g) in dry ethanol (100 mL) was added p-toluenesulfonic acid (0.315 g) followed by triethyl orthoformate (11.01 mL, 9.81 g). The suspension was stirred at 45° C. until a clear solution resulted and then maintained at 45° C. for 45 min. The solvent was removed under vacuum and then the mixture was diluted with ethyl acetate and then washed with saturated sodium carbonate solution, brine and then dried over anhydrous sodium sulfate, filtered and evaporated to give the title product (12.6 g).

Compound 6: 3-(2-formylphenyl)benzo[d]isoxazole-6-carboxylic acid

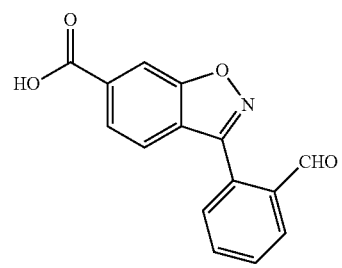 [SMILES: O=Cc1ccccc1-c1noc2cc(C(=O)O)ccc12]

To a solution of 6-bromo-3-(2-(diethoxymethyl)phenyl) benzo[d]isoxazole (Compound 5) (50 g) in dry ether (330 mL) under nitrogen at −78° C. was added a 2.5M solution of n-butyl lithium in hexanes (55.8 mL) was added dropwise and stirring continued at −78° C. for 45 min. The thick brown suspension was transferred via cannula to a mechanically stirred mixture of solid carbon dioxide pellets in ether (250 mL, under nitrogen and cooled in acetone/dry ice bath) and the resulting reaction mix topped up with further carbon dioxide pellets and left stirring in cold bath under nitrogen whilst warming to room temperature overnight. The reaction was quenched with 2N HCl (100 mL) and the ether removed under reduced pressure and ethanol (300 mL) added. The resultant yellow suspension was stirred on at 60° C. for 15 min, then cooled to room temperature and stirred in ice bath for 30 min and resulting yellow solid isolated by filtration and dried in vacuum oven at 45° C. to give the title product (29.76 g).

Compound 7: 3-(2-formylphenyl)benzo[d]isoxazole-6-carboxamide

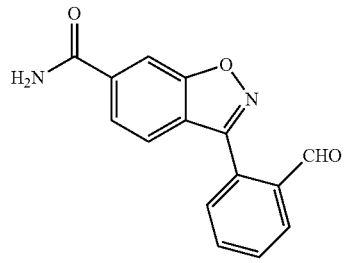 [SMILES: NC(=O)c1ccc2c(-c3ccccc3C=O)noc2c1]

To a solution of 3-(2-formylphenyl)benzo[d]isoxazole-6-carboxylic acid (Compound 6) (60.2 g) in N-methyl-2-pyrrolidinone (600 mL) at room temperature was added in one portion 1,1'-carbonyldiimidazole (40.2 g) and the solution stirred at room temperature under nitrogen for 2 h then poured into specific gravity 0.880 aqueous ammonia solution. The suspension was stirred mechanically at room temperature for 2 h then filtered. The still moist collected solid was triturated in methanol (200 mL) at room temperature then filtered, this material was triturated again with methanol (100 mL) then filtered and dried in vacuo to give the title product (54.92 g).

Compound 8: (E)-N-(2-(6-bromobenzo[d]isoxazol-3-yl)benzylidene)-1,1-bis(4-fluoro-phenyl)methanamine

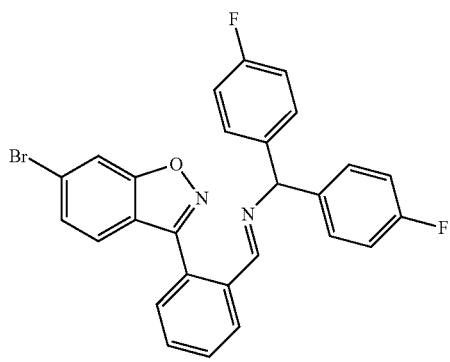 [SMILES: Fc1ccc(C(/N=C/c2ccccc2-c2noc3cc(Br)ccc23)c2ccc(F)cc2)cc1]

To a stirred solution of 2-(6-bromobenzo[d]isoxazol-3-yl)benzaldehyde (compound 7) (2 g) in dichloromethane (33 mL) was added bis(4-fluorophenyl)methanamine (1.74 g) and anhydrous magnesium sulfate and stirred under nitrogen at room temperature for 18 h. Filtration and evaporation of the filtrate and crystallisation from dichloromethane-methanol gave the title compound (2.4 g).

Compound 9: 1-(2-(6-bromobenzo[d]isoxazol-3-yl)phenyl)-2-cyclopropylethanamine

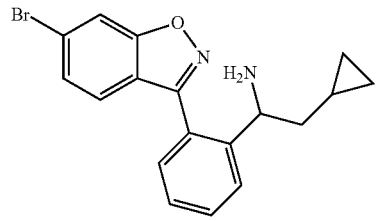 [SMILES: NC(CC1CC1)c1ccccc1-c1noc2cc(Br)ccc12]

A solution of (E)-N-(2-(6-bromobenzo[d]isoxazol-3-yl)benzylidene)-1,1-bis(4-fluorophenyl)methanamine (Compound 8) (1.34 g) in dry tetrahydrofuran (15 mL) under nitrogen was cooled to −78° C. with stirring and a 1M solution of potassium tert-butoxide in tetrahydrofuran (3.2 mL) added dropwise. Solution turned dark purple. After 20 min (iodomethyl)cyclopropane (1.45 g) was added in one portion and solution slowly warmed to room temperature, stirred at this temperature for 1.5 h then quenched by the addition of water (10 mL) and extracted with ethyl acetate. The organic extract was dried over anhydrous magnesium sulfate and evaporated to leave a dark red gum that was dissolved in acetone (20 mL) and an aqueous 2N HCl solution (15 mL) added and the mixture stirred overnight. The acetone was removed by evaporation and the aqueous solution extracted with dichloromethane. The aqueous solution was made basic with sodium bicarbonate and extracted with dichloromethane, dried over anhydrous magnesium sulfate and evaporated under reduced pressure. SCX purification (eluting with methanol then ammonia in methanol) followed by flash chromatography on silica eluting with 0 to 5% methanol in dichloromethane gave the title product (0.39 g).

Compound 10: 3-(2-((E)-((S)-tert-butylsulfinylimino)methyl)phenyl)benzo[d]isoxazole-6-carboxamide

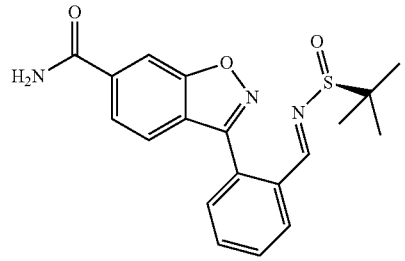 [SMILES: CC(C)(C)[S@](=O)/N=C/c1ccccc1-c1noc2cc(C(N)=O)ccc12]

To a suspension of 3-(2-formylphenyl)benzo[d]isoxazole-6-carboxamide (Compound 7) (4.12 g) in tetrahydrofuran (50 mL) was added (S)-(−)-t-butylsulfinamide (1.97 g) followed by titanium (IV) ethoxide (4.8 mL). The mixture was stirred for three days then poured onto stirred ice-water (200 mL) and ethyl acetate (200 mL) added and filtered through dicalite and the plug of solid was washed with hot ethyl acetate (200 mL), the organic layer was dried over anhydrous magnesium sulfate and evaporated to give the title compound (5.7 g) as a partially solidified gum.

In a similar manner were prepared the following:

Compound 11a: (S,E)-N-(2-(6-bromobenzo[d]isoxazol-3-yl)benzylidene)-2-methylpropane-2-sulfinamide starting from 2-(6-bromobenzo[d]isoxazol-3-yl)benzaldehyde (Compound 4a).

Compound 11 b: (S,E)-N-(2-(7-bromobenzo[d]isoxazol-3-yl)benzylidene)-2-methylpropane-2-sulfinamide starting from 2-(7-bromobenzo[d]isoxazol-3-yl)benzaldehyde (Compound 4b).

Compound 12: 3-(2-((S)-1-((S)-1,1-dimethylethylsulfinamido)-2-(pyridin-2-yl)ethyl)phenyl)benzo[d]isoxazole-6-carboxamide

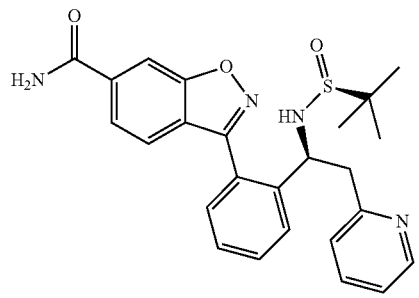 [SMILES: CC(C)(C)[S@](=O)N[C@@H](Cc1ccccn1)c1ccccc1-c1noc2cc(C(N)=O)ccc12]

To a solution of 2-picoline (22.6 mL, 21.3 g) in tetrahydrofuran (280 mL) cooled under nitrogen to −72° C. was added a 2.5M in hexanes solution of n-butyl lithium (98 mL) dropwise over 40 min keeping the internal temperature less than −70° C. The mixture was stirred at this temp for 45 min then a solution of 3-(2-((E)-((S)-tert-butylsulfinylimino)methyl)phenyl)benzo[d]isoxazole-6-carboxamide (Compound 10) (28.2 g) in tetrahydrofuran (280 mL) was added dropwise over 45 min (the internal temperature less than −70° C.) then stirred at this temp for 30 min. Reaction mixture allowed to warm to −30° C. and saturated aqueous ammonium chloride (500 mL) added. The layers were separated and aqueous layer washed with ether (3×300 mL). The combined organic extracts were washed with brine, dried over anhydrous sodium sulfate and the solvents removed. Flash chromatography on silica eluting with ethyl acetate then 1 to 5% methanol in ethyl acetate gave three fractions of product that were crystallised from the minimum of ethyl acetate to give the title product (17.2 g).

In a similar manner were prepared the following:

Compound 13: 3-(2((S)-1-((S)-1,1-dimethylethylsulfinamido)-2-phenylethyl)phenyl)benzo[d]isoxazole-6-carboxamide starting from 3-(2-((E)-((S)-tert-butylsulfinylimino)methyl)phenyl)benzo[d]isoxazole-6-carboxamide (Compound 10) and benzyl magnesium chloride.

Compound 14a: (S)—N-((1S)-1-(2-(6-bromobenzo[d]isoxazol-3-yl)phenyl)-2-(pyridin-2-yl)ethyl)-2-methylpropane-2-sulfinamide starting from (S,E)-N-(2-(6-bromobenzo[d]isoxazol-3-yl)benzylidene)-2-methylpropane-2-sulfinamide (Compound 11a) and 2-picoline.

Compound 14b: (S)—N-((1S)-1-(2-(7-bromobenzo[d]isoxazol-3-yl)phenyl)-2-(pyridin-2-yl)ethyl)-2-methylpropane-2-sulfinamide starting from (S,E)-N-(2-(7-bromobenzo[d]isoxazol-3-yl)benzylidene)-2-methylpropane-2-sulfinamide (Compound 11 b) and 2-picoline.

Compound 15a: 1-(S)-(2-(6-bromobenzo[d]isoxazol-3-yl)phenyl)-2-(pyridin-2-yl)ethanamine

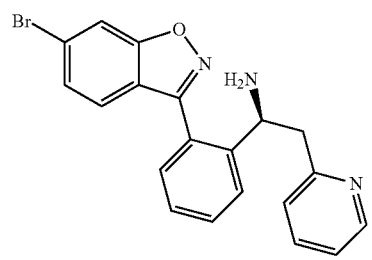 [SMILES: N[C@@H](Cc1ccccn1)c1ccccc1-c1noc2cc(Br)ccc12]

To a solution of (S)—N-((1S)-1-(2-(6-bromobenzo[d]isoxazol-3-yl)phenyl)-2-(pyridin-2-yl)ethyl)-2-methylpropane-2-sulfinamide (Compound 14a) (1.76 g) dissolved in dichloromethane (10 mL) was added 2N hydrochloric acid (10 mL) and the mixture left to stand at room temperature. The resulting mixture was taken up in methanol and loaded onto a 20 g SCX column and eluted with neat methanol, followed by ammonia-methanol and the fractions containing product were evaporated to give the title product (1.25 g) as a clear yellow oil.

In a similar manner was prepared:

Compound 15b: 1-(S)-(2-(7-bromobenzo[d]isoxazol-3-yl)phenyl)-2-(pyridin-2-yl)ethanamine starting from (S)—N-((1S)-1-(2-(6-bromobenzo[d]isoxazol-3-yl)phenyl)-2-(pyridin-2-yl)ethyl)-2-methylpropane-2-sulfinamide (Compound 14b).

Compound 16a: tert-butyl 1-(S)-(2-(6-bromobenz[d]isoxazol-3-yl)phenyl)-2-(pyridin-2-yl)ethylcarbamate

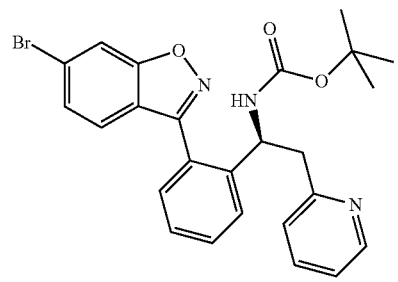 [SMILES: CC(C)(C)OC(=O)N[C@@H](Cc1ccccn1)c1ccccc1-c1noc2cc(Br)ccc12]

To solution of 1-(S)-(2-(6-bromobenzo[d]isoxazol-3-yl)phenyl)-2-(pyridin-2-yl)ethanamine (Compound 15a) (2.13 g) in dry dichloromethane (10 mL) was added di-tert-butyl dicarbonate (1.24 g) and the solution stirred at ambient temperature over two days. An aqueous solution of 0.5M citric acid was added and the reaction mixture extracted with dichloromethane, the extracts washed with brine, dried over anhydrous sodium sulfate, filtered and evaporated to give a dark brown oil that was purified on 40 g silica column eluting with 25% ethyl acetate in heptane to give the title product (1.72 g)

In a similar manner was prepared:

Compound 16b: tert-butyl 1-(S)-(2-(7-bromobenzo[d]isoxazol-3-yl)phenyl)-2-(pyridin-2-yl)ethylcarbamate starting from 1-(S)-(2-(7-bromobenzo[d]isoxazol-3-yl)phenyl)-2-(pyridin-2-yl)ethanamine (Compound 15b).

Compound 17: tert-butyl 1-(2-(6-bromobenzo[d]isoxazol-3-yl)phenyl)-2-cyclopropylethylcarbamate starting from 1-(2-(6-bromobenzo[d]isoxazol-3-yl)phenyl)-2-cyclopropylethanamine (Compound 9)

Compound 18a: 3-(2-(1-(S)-(tert-butoxycarbonylamino)-2-(pyridin-2-yl)ethyl)phenyl) benzo[d]isoxazole-6-carboxylic acid

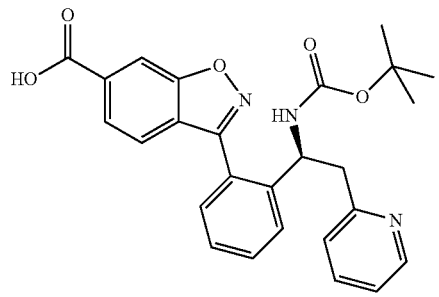 [SMILES: CC(C)(C)OC(=O)N[C@@H](Cc1ccccn1)c1ccccc1-c1noc2cc(C(=O)O)ccc12]

To a solution of tert-butyl 1-(S)-(2-(6-bromobenzo[d]isoxazol-3-yl)phenyl)-2-(pyridin-2-yl)ethylcarbamate (Compound 16a) (1.72 g) in diethyl ether (30 mL) at 5° C. was added a 60% dispersion in mineral oil of sodium hydride (3.34 g). The suspension was stirred at 5° C. for 10 min and then cooled to −65° C. and a 2.5M solution of n-butyllithium in hexanes (5.57 mL) was added. The suspension was stirred at −70° C. for 30 min and then poured onto solid carbon dioxide pellets and left to stand until the mixture reached room temperature. To this was added water and acidified with citric acid and extracted with ether (3×200 mL), the organic layers were dried over anhydrous magnesium sulfate and evaporated. Flash chromatography eluting with 10% methanol in dichloromethane to give the title product (0.71 g).

In a similar manner was prepared:

Compound 18b: 3-(2-(1-(S)-(tert-butoxycarbonylamino)-2-(pyridin-2-yl)ethyl)phenyl) benzo[d]isoxazole-7-carboxylic acid starting from tert-butyl 1-(S)-(2-(7-bromobenzo[d]isoxazol-3-yl)phenyl)-2-(pyridin-2-yl)ethylcarbamate (Compound 16b).

Compound 19: 3-(2-(1-(tert-butoxycarbonylamino)-2-cyclopropylethyl)phenyl) -benzo[d]isoxazole-6-carboxylic acid starting from tert-butyl 1-(2-(6-bromobenzo[d]isoxazol-3-yl)phenyl)-2-cyclopropylethylcarbamate (Compound 17).

Compound 20a: tert-butyl 1-(S)-(2-(6-(chlorocarbonyl)benzo[d]isoxazol-3-yl)phenyl)-2-(pyridin-2-yl)ethylcarbamate

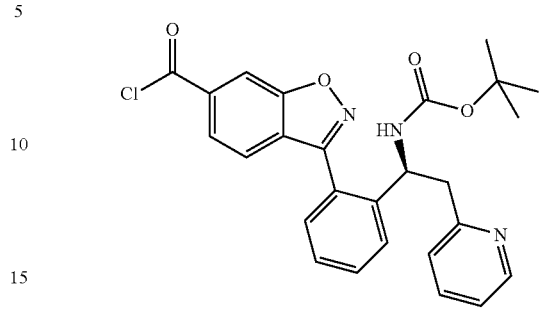

To a solution of 3-(2-(1(S)-(tert-butoxycarbonylamino)-2-(pyridin-2-yl)ethyl) -phenyl)benzo[d]isoxazole-6-carboxylic acid (Compound 18a) (45 mg) dissolved in dry dichloromethane (2 mL) under nitrogen, cooled with ice bath, was added triethylamine (127 μL) then thionyl chloride (35.5 μL). After 10 min the solvents were removed under reduced pressure to give the title product.

In a similar manner was prepared:

Compound 20b: tert-butyl 1-(S)-(2-(7-(chlorocarbonyl)benzo[d]isoxazol-3-yl)phenyl)-2-(pyridin-2-yl)ethylcarbamate starting from 3-(2-(1-(S)-(tert-butoxycarbonylamino)-2-(pyridin-2-yl)ethyl)phenyl)benzo[d]isoxazole-7-carboxylic acid (Compound 18b).

Compound 21: tert-butyl 1-(2-(6-(chlorocarbonyl)benzo[d]isoxazol-3-yl)phenyl)-2-cyclopropylethylcarbamate starting from 3-(2-(1-(tert-butoxycarbonylamino)-2-cyclopropylethyl)phenyl)benzo[d]isoxazole-6-carboxylic acid (Compound 19)

Compound 22: Methyl 3-(2-(1-(S)-amino-2-(pyridin-2-yl)ethyl)phenyl)benzo[d]isoxazole-7-carboxylate

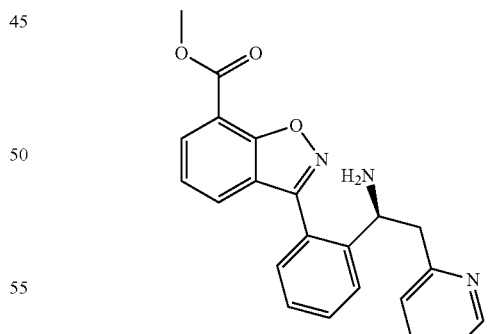

To a solution of (S,E)-N-(2-(7-bromobenzo[d]isoxazol-3-yl)benzylidene)-2-methyl -propane-2-sulfinamide (Compound 11b) (145 mg) dissolved in dry methanol (1 mL) and dry N,N-dimethylformamide (3 mL) was added 1,1'-bis(diphenylphosphino)ferrocene-dichloropalladium (II) (42 mg), 1,1'-bis(diphenylphosphino)ferrocene (32 mg) and triethylamine (0.2 mL). The solution was stirred at 80 to 90° C. under an atmosphere of carbon monoxide gas overnight. Flash chromatography eluting with 0 to 5% methanol in dichloromethane followed by evaporation, treatment with 2N HCl in ether (1 mL) for 10 minutes then purification by SCX chromatography eluting with methanol then ammonia in methanol followed by flash chromatography eluting with 2 to 10% methanol in dichloromethane gave the title compound (22 mg).

EXAMPLE 1

3-(2-(1-(S)-amino-2-(pyridin-2-yl)ethyl)phenyl) benzo[d]isoxazole-6-carboxamide L-(+)-tartrate salt

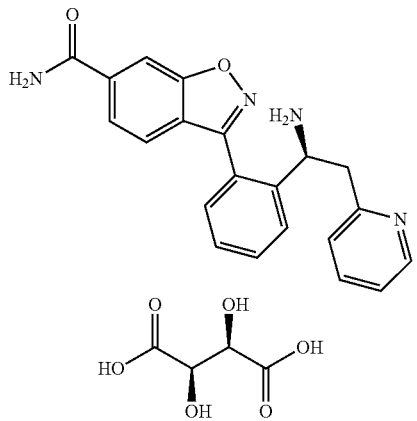

To a solution of 3-(2-((S)-1-((S)-1,1-dimethylethylsulfinamido)-2-(pyridin-2-yl) -ethyl)phenyl)benzo[d]isoxazole-6-carboxamide (Compound 12) (63 g) in methanol (700 mL) was added 2N HCl in diethyl ether (350 mL) in one portion. The solution was stirred at room temperature for 2.5 h then ether (2 ) added followed by saturated aqueous sodium carbonate solution (ca 1.5 ) to approximately pH 10. The layers were separated and the aqueous solution extracted with ether (×6) then dichloromethane(×3) and the combined organic fractions dried over anhydrous sodium sulfate and the solvents removed under reduced pressure to give a yellow foam that was chromatographed on silica (800 g) eluting with ethyl acetate-methanol-7M ammonia in methanol (90:10:0.3) to give 35 g of a white foam that was converted to the L-(+)-tartrate salt and crystallised from ethanol to give the title compound (52 g), MS (ES): m/z 359 [M+H]$^+$; $[\alpha]_D$, (MeOH, c=4.4)+8.4.

In a similar manner was prepared the following:

EXAMPLE 2

3-(2-((S)-1-amino-2-phenylethyl)phenyl)benzo[d]isoxazole-6-carboxamide hydrochloride salt starting from 3-(2-((S)-1-((S)-1,1-dimethylethylsulfinamido)-2-phenylethyl)phenyl)benzo[d]isoxazole-6-carboxamide (Compound 13), MS (ES): m/z 358 [M+H]$^+$; $[\alpha]_D$ (MeOH, c=2.1)+34.3.

EXAMPLE 3

3-(2-(1-(S)-amino-2-(pyridin-2-yl)ethyl)phenyl)-N,N-dimethylbenzo[d]isoxazole-6-carboxamide L-(+)-tartrate salt

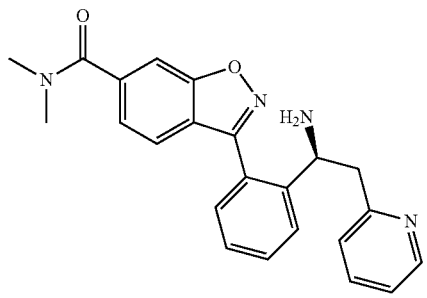

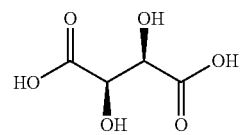

To a stirred solution of tert-butyl 1-(S)-(2-(6-(chlorocarbonyl)benzo[d]isoxazol-3-yl)phenyl)-2-(pyridin-2-yl)ethylcarbamate (Compound 20a) dissolved in dry dichloromethane (2 mL) with ice bath cooling was added an excess of dimethylamine (2M in tetrahydrofuran) then the reaction was warmed to room temperature. After 1 h the solvent was removed under reduced pressure and the residue purified by flash chromatography eluting with 1 to 4% methanol in dichloromethane. The pure fractions of the tertiary amide were evaporated then dissolved in dichloromethane (2.5 mL) and treated with trifluoroacetic acid (0.5 mL). Evaporation and purification by SCX chromatography eluting with methanol then ammonia in methanol gave 207 mg of the amine free base that was treated with L-(+)-tartaric acid to give the title compound (16 mg), MS (ES): m/z 387 [M+H]$^+$.

In a similar manner were prepared:

Compound 23: 3-(2-(1-amino-2-cyclopropylethyl) phenyl)benzo[d]isoxazole-6-carboxamide starting from tert-butyl 1-(2-(6-(chlorocarbonyl)benzo[d] isoxazol-3-yl)phenyl)-2-cyclopropylethyl carbamate (Compound 21) and ammonia

EXAMPLE 4

3-(2-(1-(S)-amino-2-(pyridin-2-yl)ethyl)phenyl)-N,N-dimethylbenzo[d]isoxazole-7-carboxamide L-(+)-tartrate salt starting from tert-butyl 1-(S)-(2-(7-(chlorocarbonyl)benzo[d]isoxazol-3-yl)phenyl)-2-(pyridin-2-yl)ethylcarbamate (Compound 20b)

EXAMPLE 5

3-(2-(1-(S)-amino-2-cyclopropylethyl)phenyl)benzo[d]isoxazole-6-carboxamide L-(+)-tartrate salt

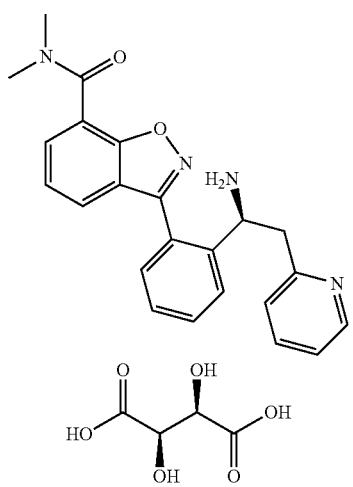

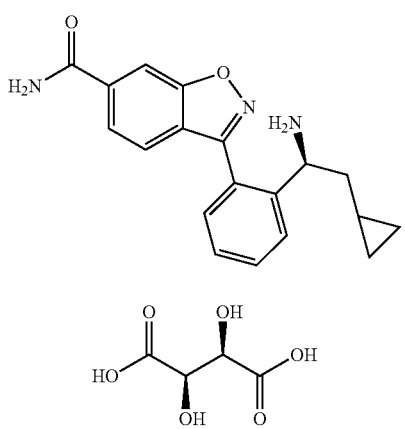

3-(2-(1-amino-2-cyclopropylethyl)phenyl)benzo[d]isoxazole-6-carboxamide (Compound 23) (280 mg) was dissolved in methanol (50 mL) separated into the component enantiomers by SFC preparative chromatography (40 mL/min, 220 nm detection, 35° C., 100 Bar on ADH column with 25% Isopropanol/0.1% Isopropylamine as modifier). Conversion of the free base of the first eluting peak to the L-(+)-tartrate salt gave the title compound (73 mg), MS (ES): m/z 359 [M+H]$^+$. This enantiomer is the first eluting peak when compared to racemate using analytical SFC chromatography (100 bar, 4 ml/min, 25% Isopropanol/0.1% Isopropylamine, 35° C., Chiralpak AD-H 25 cm×0.46 cm column, 220 nm UV detection).

EXAMPLE 6

3-(2-(1-(S)-amino-2-(pyridin-2-yl)ethyl)phenyl)benzo[d]isoxazole-7-carboxamide L-(+)- tartrate salt

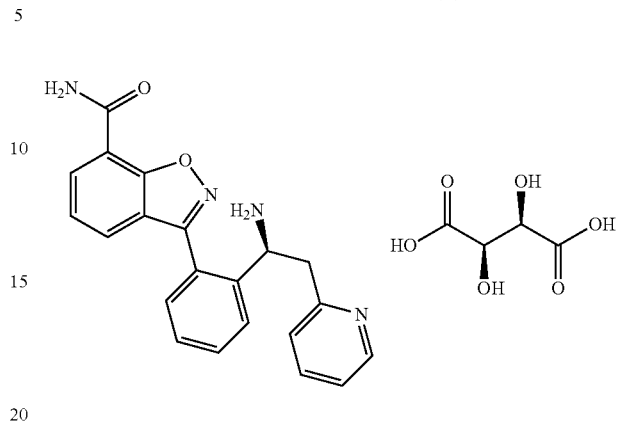

A solution of methyl 3-(2-(1-(S)-amino-2-(pyridin-2-yl)ethyl)phenyl)benzo-[d]isoxazole-7-carboxylate (Compound 22) (22 mg) a 7M ammonia in methanol solution (1 mL) was placed in a sealed tube and stirred at 75° C. for 4 days then evaporated under reduced pressure and purified by flash chromatography eluting with 3 to 8% methanol in dichloromethane followed by conversion to the L-(+)-tartrate salt to give the title compound (17 mg) MS (ES): m/z 359 [M+H]$^+$.

EXAMPLE 7

Biological Testing Using Automated Patch Clamp Electrophysiology

A: Cell Culture

HEK-hHCN1-2H10 cells were cultured in 225 cm$^2$ flasks, in MEM (with Earle's salts) supplemented with 10% Fetalclone II+0.1 mM non essential amino acids+1 mM sodium pyruvate+10 mM HEPES+0.5 mg/mL G418. The cells were routinely maintained at 37° C. in an atmosphere of 5% CO$_2$ and 100% relative humidity until 50% confluent. 24 hours before use, cells were incubated at 30° C. to increase HCN1 membrane expression and harvested immediately prior to patch clamp experiments. The growth medium was aspirated under vacuum and the cells are washed in 50 mL Dulbecco's Phosphate Buffered Saline (without CaCl$_2$ and MgCl$_2$; D-PBS). The cells are then dissociated by incubating with 5 mL of a 1:1 mixture of 0.1% Trypsin/0.04% EDTA and cell dissociation buffer (CDS), at 37° C. for 2 minutes. Cell dissociation was terminated by the addition of 5 mL growth medium after which, the cells were mechanically dissociated by gently triturating 3-4 times using a 10 mL pipette. The cells were counted using a haemocytometer, recovered by centrifugation at 212 g for 1½ minutes and resuspended in 5 mLs of filtered external recording solution (see below). The cells were re-covered again by centrifugation as above and resuspended in filtered extracellular solution at a density of 2×10$^6$ cells per mL, triturating 4-5 times. The cells were transferred immediately to IonWorks.

B: Patch Clamp Recordings

Automated patch clamp recordings were performed using the IonWorks Quattro (MDS Analytical Technologies). The IonWorks Quattro was primed with intracellular (in mM: KGluconate, 130; NaCl, 10; MgCl$_2$, 1; EGTA, 1; HEPES, 10, pH 7.35) and extracellular solution (in mM: NaGluconate, 104; NaCl, 10; KCl, 30; MgCl$_2$, 1; CaCl$_2$, 1.8; Hepes, 10; glucose, 5; pH 7.35) recording solutions. Perforated patch clamp recordings were established with 0.1 mg/mL amphotericin B (in 0.36% DMSO) and the cells voltage clamped at −40 mV. Whole cell perforated patch clamp recordings were performed in two separate runs, with voltage steps to −80 mV and −120 mV for 1 s; leak subtraction was performed using a −10 mV voltage pulse prior to channel activation. Compounds were tested at 12 concentrations (half log intervals; 1% DMSO) and incubated for 10 minutes between current recordings. Cells were excluded with whole cell currents less 100 pS, seal resistances <50 MΩ or if the seal resistance varied by >50% during the course of the experiment. The amplitude of the time-dependent currents mediated by HCN, both pre- and post compound addition, was measured as the difference between the current recorded immediately after the capacity transient on stepping to the test voltage and the current measured after it had reached a steady state amplitude. Data were processed using the IonWorks Quattro System Software version 2 and analysed in Activity Base with XLFit 4.1, using a standard 4 parameter logistic function. Concentration response curves were generated and compound potency at the hHCN1 channel reported as the $pEC_{50}$, with the appropriate confidence intervals. Compounds of the invention have a $pEC_{50}$ activity of greater than 4 at the −80 mV voltage step and preferred compounds of the invention have a $pEC_{50}$ activity greater than 5 at the −80 mV voltage step.

EXAMPLE 8

The Rat (Chung) Model of Neuropathic Pain

In this model, mechanical allodynia is induced by tight ligation of the left L5 spinal nerve. This assay has been employed successfully to demonstrate anti-allodynic effects of anticonvulsants (gabapentin), antidepressants (duloxetine) and opioid analgesics (morphine) which are used clinically in the treatment of neuropathic pain.

Male Wistar rats (228-301 g body weight at time of surgery) were employed in the study. Rats were placed on an elevated (~40 cm) mesh floor in perspex boxes and the rats' withdrawal threshold to a mechanical stimulus (calibrated von Frey filaments) was measured using filaments of increasing force (2.6-167 mN). The von Frey filaments were applied to the plantar surface of the paw and threshold response determined using the up and down method (Chaplan S. R. et al., J. Neurosci. Methods 53: 55-63, 1994; Dixon. J. Ann.Rev.Pharmacol.toxicol. 20: 441-462, 1980). A positive response was noted if the paw was sharply withdrawn. A cut-off of 15 g was selected as the upper limit for testing. Following baseline measurements each animal was anaesthetised and the L5 spinal nerve tightly ligated. The animals were allowed to recover from the surgery for a period of at least three days. On the day of drug administration the paw withdrawal thresholds were re-measured (0 min). Immediately after this reading, the rats were dosed orally with vehicle or test compound and readings measured at various time points after compound administration.

Data were expressed as mean±s.e.m. Statistical analysis was performed using the Kruskal-Wallis one-way analysis of variance, a non-parametric statistical test. Each of the treatment groups were then compared against the vehicle group, using the non-parametric Dunn's test. The $ED_{50}$ (dose at which allodynia is reversed by approximately 50%) value was also calculated at $t_{max}$ using linear regression (sigmoidal dose response; variable slope) with constants of 0 and 15 g (cut-off) for the bottom and top, respectively (XLFit software).

The invention claimed is:
1. A 2-(1,2-benzisoxazol-3-yl)benzylamine compound having the Formula I

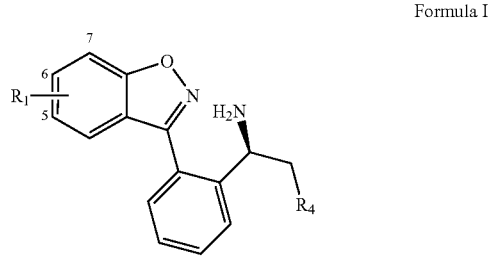

Formula I wherein
R₁ represents the group CONR₂R₃ which is present at one of the positions 5-, 6- or 7- on the 1,2-benzisoxazole ring;
R₂ and R₃ are independently H or (C₁₋₄)alkyl; and
R₄ is cyclopropyl, 2-pyridyl or phenyl, optionally substituted with one or more halogens;
or a pharmaceutically acceptable salt thereof.

2. The 2-(1,2-benzisoxazol-3-yl)benzylamine compound of claim 1 or a pharmaceutically acceptable salt thereof, wherein R₄ is cyclopropyl.

3. The 2-(1,2-benzisoxazol-3-yl)benzylamine compound of claim 1 or a pharmaceutically acceptable salt thereof, wherein R₄ is 2-pyridyl.

4. The 2-(1,2-benzisoxazol-3-yl)benzylamine compound of claim 1 or a pharmaceutically acceptable salt thereof, wherein R₄ is phenyl, optionally substituted with one or more halogens.

5. The 2-(1,2-benzisoxazol-3-yl)benzylamine compound of claim 1 or a pharmaceutically acceptable salt thereof, wherein R₁ represents the group CONR₂R₃ at the 6-position on the 1,2-benzisoxazole ring.

6. The 2-(1,2-benzisoxazol-3-yl)benzylamine compound of claim 5 or a pharmaceutically acceptable salt thereof, wherein R₂ and R₃ are both methyl or hydrogen.

7. The 2-(1,2-benzisoxazol-3-yl)benzylamine compound of claim 1 which is selected from:
3-(2-(1-(S)-amino-2-(pyridin-2-yl)ethyl)phenyl)benzo[d]isoxazole-6-carboxamide;
3-(2-((S)-1-amino-2-phenylethyl)phenyl)benzo[d]isoxazole-6-carboxamide;
3-(2-(1-(S)-amino-2-(pyridin-2-yl)ethyl)phenyl)-N,N-dimethylbenzo[d]isoxazole-6-carboxamide;
3-(2-(1-(S)-amino-2-(pyridin-2-yl)ethyl)phenyl)-N,N-dimethylbenzo[d]isoxazole-7-carboxamide;
3-(2-(1-(S)-amino-2-cyclopropylethyl)phenyl)benzo[d]isoxazole-6-carboxamide; and
3-(2-(1-(S)-amino-2-(pyridin-2-yl)ethyl)phenyl)benzo[d]isoxazole-7-carboxamide;
or a pharmaceutically acceptable salt thereof.

8. A pharmaceutical composition comprising a 2-(1,2-benzisoxazol-3-yl)benzylamine compound of claim 1 or a pharmaceutically acceptable salt thereof in admixture with pharmaceutically acceptable auxiliaries.

9. A pharmaceutical composition comprising a 2-(1,2-benzisoxazol-3-yl)benzylamine compound of claim 7 or a pharmaceutically acceptable salt thereof in admixture with pharmaceutically acceptable auxiliaries.

10. A method of treatment of pain which is mediated through modulation of the $I_h$ channel, the method comprising administering to a patient in need thereof a therapeutically effective amount of a 2-(1,2-benzisoxazol-3-yl)benzylamine compound of claim 1 or a pharmaceutically acceptable salt thereof.

11. The method of claim 10, wherein the pain is neuropathic pain.

12. The method of claim 10, wherein the pain is inflammatory pain.

* * * * *